US006955818B1

(12) United States Patent  
Hacket et al.

(10) Patent No.: US 6,955,818 B1  
(45) Date of Patent: Oct. 18, 2005

(54) POUR-ON FORMULATIONS

(75) Inventors: Kristina Clare Hacket, North Sydney (AU); Lionel Barry Low, Dural (AU); James Terence Rothwell, South Turramurra (AU)

(73) Assignee: Eli Lilly and Company, Indianapolis, IN (US)

( * ) Notice: Subject to any disclaimer, the term of this patent is extended or adjusted under 35 U.S.C. 154(b) by 490 days.

(21) Appl. No.: 10/130,315

(22) PCT Filed: Nov. 17, 2000

(86) PCT No.: PCT/US00/30143

§ 371 (c)(1),  
(2), (4) Date: May 13, 2002

(87) PCT Pub. No.: WO01/40446

PCT Pub. Date: Jun. 7, 2001

(30) Foreign Application Priority Data

Dec. 2, 1999 (AU) .................................. PQ4416

(51) Int. Cl.⁷ ......................... A01N 25/00; A01K 29/00
(52) U.S. Cl. ..................... 424/405; 514/938; 514/941; 514/943; 119/600; 119/650; 119/652; 119/653
(58) Field of Search ................. 424/405; 514/341, 514/406, 407, 943, 938; 119/600, 603, 650, 119/652, 653

(56) References Cited

U.S. PATENT DOCUMENTS

| | | | |
|---|---|---|---|
| 5,059,593 A | 10/1991 | Standel et al. | |
| 5,145,684 A | 9/1992 | Liversidge et al. | |
| 5,202,242 A | 4/1993 | Mynderse et al. | |
| 5,227,295 A | 7/1993 | Baker | |
| 5,362,634 A | 11/1994 | Boeck et al. | |
| 5,496,931 A | 3/1996 | Boeck et al. | |
| 5,539,089 A | 7/1996 | Broughton et al. | |
| 5,571,901 A | 11/1996 | Boeck et al. | |
| 5,591,606 A | 1/1997 | Turner et al. | |
| 5,631,155 A | 5/1997 | Turner et al. | |
| 5,670,364 A | 9/1997 | Mynderse et al. | |
| 5,670,486 A | 9/1997 | Mynderse et al. | |
| 5,767,253 A | 6/1998 | Turner et al. | |
| 5,840,861 A | 11/1998 | Mynderse et al. | |
| 5,880,076 A | * 3/1999 | Vermeer | ..................... 510/123 |
| 6,001,981 A | 12/1999 | DeAmicis et al. | |
| 6,010,710 A | 1/2000 | Elchegaray et al. | |
| 6,022,559 A | * 2/2000 | Simonnet | .................... 424/450 |
| 6,063,771 A | * 5/2000 | Snyder | ........................ 514/31 |
| 6,096,326 A | * 8/2000 | Wikholm | .................... 424/401 |
| 6,342,482 B1 | 1/2002 | Snyder | |

FOREIGN PATENT DOCUMENTS

| | | | | |
|---|---|---|---|---|
| CA | 2059602 | 7/1992 | | |
| DE | 35 31 920 | 3/1987 | | |
| EP | 0 069 269 | 6/1982 | | |
| EP | 0 375 316 | 12/1989 | | |
| GB | 2 135 886 | 9/1984 | | |
| GB | 2135886 A | * 9/1984 | ......... | A01N 25/02 |
| GB | 2 317 564 | 4/1998 | | |
| GB | 2317564 A | * 4/1998 | ......... | A01N 47/02 |
| WO | WO 94/26113 | 11/1994 | | |
| WO | WO 97/00265 | 1/1997 | | |
| WO | WO 97/12521 | 4/1997 | | |
| WO | WO 97/33471 | 9/1997 | | |
| WO | WO 00/01347 | 6/1999 | | |
| WO | WO 00/30449 | 6/2000 | | |
| WO | WO 01/12156 | 7/2000 | | |
| WO | WO 00/60940 | 10/2000 | | |
| WO | WO 01/11961 | 2/2001 | | |
| WO | WO 01/11962 | 2/2001 | | |
| WO | WO 01/11963 | 2/2001 | | |
| WO | WO 01/11964 | 2/2001 | | |
| WO | WO 01/19840 | 3/2001 | | |

OTHER PUBLICATIONS

DeAmics, et al., "Physical and Biological Properties of the Spinosyns: Novel Macrolide Pest-Control Agents from Fermentation," American Chemical Society, Chapter 11 (1997).
Spinosad Technical Guide.
Boech, et al., Chemical Abstracts, 114, 9, Abstract No. 80066m (1991).
Kirst, et al., "Discovery Isolation, and Structure Elucidation of a Family of Structurally Unique, Fermentation-Derived Tetracyclic Macrolides," ACS Symposium Series, Snythesis and Chemistry of Agrochemicals III, 504, pp. 214-225 (1992).
Crouse, et al., "Naturally Derived Materials as Products and Leads for Insect Control: The Spinosyns," Rev. Toxicol, 2, pp. 133-146 (1998).

(Continued)

*Primary Examiner*—Thurman K. Page
*Assistant Examiner*—Micah-Paul Young
(74) *Attorney, Agent, or Firm*—John C. Demeter

(57) ABSTRACT

A non-irritant topically acceptable carrier selected from the group consisting of: a) i) at least one of tripropylene glycol methyl ether and dipropylene glycol methyl ether, and ii) at least one of alcohol, wool grease and propylene glycol, wherein (i) is present in an amount of at least about 60% wt of the carrier; b) i) at least one of octyl palmitate, octyl stearate and glyceryl tri caprylate/caprate, and ii) at least one of dioctyl succinate, isopropyl myristate, cetearyl octanoate, propylene glycol 2 myristyl ether propionate, isopropyl palmitate, isopropyl laurate, isocetyl stearate, oleic acid and methyl oleate, and optionally including iii) at least one of alcohol, wool grease and propylene glycol, wherein (ii) is present in an amount of up to about 40% wt of the carrier; and c) i) at least one of octyl palmitate, octyl stearate and glyceryl tri caprylate/caprate, and ii) at least one of alcohol, wool grease and propylene glycol, wherein (i) is present in an amount of at least about 60% wt of the carrier.

33 Claims, No Drawings

OTHER PUBLICATIONS

Mertz, F. P., et al., "Saccharopolyspora spinosad sp. Nov. Isolated from Soil Collected in a Sugar Mill Rum Still," Int. J. System Bacteriol, 40, pp. 34-39 (1990).

Salgado, V. L., "Studies on the Mode of Action of Spinosad: Insect Symptoms and Physiological Correlates," Pestic. Biochem. Physiol., 60, pp. 91-102 (1998).

Thompson, G. D., et al., "Spinosad A Case Study: An Example from a Natural Products Discovery Programme," Pest. Manag. Sci., 56, pp. 696-702 (2000).

Thompson, G. D., "The Discovery of Saccharopolyspora spinosad and a New Class of Insect Control Products," Down to Earth, 52, pp. 1-5 (1997).

Breuninger, J. M., "Conserve SC: A New Product for the Turfgrass and Ornamental Industry," Down to Earth, 53, pp. 1-5 (1998).

Nolting, S. P., "Insect Control in Cotton with Tracer," Down to Earth, 52, pp. 21-27 (1997).

Sparks, et al., "Biological Activity of the Spinosyns, New Fermentation Derived Insect Control Agents, on Tobaco Budworm (Lepidopters: Noctuidae) Larvae," J. Econ. Entomol., 91, pp. 1277-1283 (1996).

Sparks, T. C., et al., "Biological Characteristics of the Spinosyns: A New Class of Naturally Derived Insect Control Agents," In: Proceedings of the 1995 Beltwide Cotton Production Conference, National Cotton Counsil, Memphis, TN, 903-907 (1995).

Kirst, et al., Tetrahydron Letters, 32(37), 4839-4842 (1991).

Snyder, et al., J. Chem. Soc., 106, 787-789 (1984).

Thompson, et al., "Spinosyns: An Overview of New Natural Insect Management Systems," Proceedings of the 1995 Beltwide Cotton Production Conference, National Cotton Council, Memphis, TN, 1039-1043 (1995).

Agricultural Chemical News, 195(2), "NAF-85 (spinosad): DowElanco insecticide" (1995).

Agricultural Chemical News, 186(2), "Spinosad, NAF-144; DowElanco seeks EPA approval for insecticide" (1995).

Spencer, et al., "Spinosad insect control agent; lack of effects in a one year neurotoxicity screening study in rats," Fundam. Appl. Tocicol.; Pt. 2, 211, 30(1) (1996).

Kirst, et al., "Chemistry of Biology of the spinosyns a new class of naturally derived insect control agents," Abstracts of Papers Americal Chemical Society; 210th American Chemical Society, 210, Part 1, Abstract No. AGRO061.

Adan, et al., "Laboratory evaluation of the novel naturally derived compound spinosad against ceratitis capitata," Pesticide Science, 48(3), pp. 261-268 (1996).

Boyd, Impact of insecticides on predators of the soybean looper, pseudoplusia inc, PhD Dissertation, The Louisiana State University and Agricultural and Mechanical Col., UMI (9637762).

King, et al., Spinosad bait for the Caribbean fruit fly (Kiptera: Tephritidea), Florida Entomologist, 79(4) pp. 526-531 (1996); ISSN: 0015-4040.

Magnussen, et al., "Characterization of spinosad related residues in poultry tissues and eggs following oral administration," 211th American Chemical Society National Meeting, New Orleans, Louisiana, USA, 211:1-2; AGRO 43; ISSN 0065-7 (1996).

Saunders, et al., "Degradation of spinosad in aqueous solution," 211th Americal Chemical Society National Meeting, New Orleans, Louisiana, USA, 211, Part 1, Abstract No. AGR0048.

Sparks, et al., "Chemistry and biology of the spinosyns: components of spinosad (Tracer), the first entry into DowElanco's naturalyte class of insect control products," Proc.—Beltwide Cotton Conf., 2:692-696 (1996); ISSN: 1059-2644.

Burton, et al., "Tracer naturalyte insect control physical property attributes," Proc.—Beltwide Cotton Conf., 2:696-697 (1996); ISSN: 1059-2644.

Thompson, et al., "Spinosad and the new naturalyte insect control class," Proc.—Beltwide Cotton Conf., 2:870-872 (1996); ISSN: 1059-2644.

Murray, et al., "The effects of spinosad (Tracer) on pests and beneficials," Australian Cottongrower, 18:62-64 (1997).

Heller, et al., "Evaluation of experimental DowElanco NAF85 and NAF127 formulations, and Dursban Pro for management of black cutworm on creeping bentgrass, 1996," Anthropod Management Tests, 22:345 (1997).

Heller, et al., "Evaluation of NAF formulations, Dursban Pro, and Scimitar CS for management of black cutworm on creeping bentgrass, 1995," Arthropod Management Tests, 22:346 (1997).

Salgado, et al., "Studies on the mode of action of spinosad, the active ingredient in Tracer insect control," Proc.—Beltwide Cotton Conference, 2:1082-1084 (1997); ISSN: 1059-2644.

Murrey, et al., "The effect of spinosad (Tracer) on arthropod pest and beneficial populations in Australian cotton," Proc.—Beltwide Cotton Conf., 2:1087-1091 (1997); ISSN: 1059-2644.

Sparks, et al., "Penetration and metabolism of spinosyn A in lepidopterous larvae," Proc.—Beltwide Cotton Conference, 2:1259-1264 (1997); ISSN: 1059-2644.

Agricultural Chemical News, "Success (spinosad): a new DowElanco insecticide formulation," 209: pp. 2-15 (1997).

Agricultural Chemical News, "Tracer (spinosad): DowElanco gains insecticide registration," 211; pp. 3-15 (1997).

Agricultural Chemical News, "Success (spinosad): DowElanco gains 24(c) insecticide label to use in California," 213; pp. 2-15 (1997).

Agricultural Chemical News, "Conserve SC (spinosad): DowElanco gains EPA, USA, insecticide registration," 215; pp. 1-15 (1997).

Yeh, et al., "Application of empore disc extraction for trace analysis of spinosad and metabolites in leafy vegetables, pepper, and tomatoes by high-performance liquid chromatography with ultraviolet detection," Journal of Agricultural and Food Chemistry, vol. 45, No. 5, pp. 1746-1751; ISSN 0021-8561.

Boyd, et al., "Residual toxicity of selected insecticides to heteropteran predaceous species (Heteroptera: Lygaeidae, Nabidae, Pentatomidae) on soybean," Environ. Entomol., vol. 27, No. 1, pp. 154-160 (1998).

Kolarid, et al., "Colorado potato beetle control, 1997," Arthropod Management Tests, vol. 23; pp. 124-126 (1998).

Cowles, "Effect of spinosad formulations and other miticides on twospotted spider mite, 1995," Arthropod Management Tests, vol. 23; pp. 342-343 (1998).

Kjaer, et al., "The impact of phenology, exposure and instar susceptibility on indecticide effects on a chrysomelid beetle population," Prestic. Sci., vol. 52, No. 4, pp. 361-371 (1998).

Marty, et al., "The maternal and developmental toxicity of spinosad in Sprague-dawley rats and New Zealand White rabbits," Teratology, vol. 57, pp. 4-5 (1998).

Salgado, et al., "Studies on the mode of action of spinosad: the internal effective concentration dependence of neural excitation," *Pesticide Biochemistry and Physiology*, vol. 60, No. 2, pp. 103-110 (1998).

Boyd, et al., "Susceptibility of predaceous hemipteran species to selected insecticides on soybean in Louisiana," *Journal of Economic Entomology*, vol. 91, No. 2, pp. 401-409 (1998).

Woodburn, et al., "Bioconcentration and metabolism of a unique insecticide (spinosyn) by the Rainbow trout," *Second World Congress of the Society of environmental toxicology and chemi,* PT127; pp. 5-9 (1995).

Stoltz, et al., "Colorado potato beetle control with foliar sprays, 1995," *Arthropod Management Tests*, vol. 21, pp. 168-169.

Sewell, et al., "Irish potato, control of Colorado potato beetle, 1995," *Arthropod Management Tests*, vol. 21, pp. 158-159.

Olson, et al., "Potato, Colorado potato beetle control with spinosad, 1995," *Arthropod Management Tests*, vol. 21; pp. 154-155.

Noetzel, et al., "Control of resistant Colorado potato beetle, Blaine, MN, 1995," *Arthropod Management Tests*, vol. 21, p. 149.

Noetzel, et al., "Colorado potato beetle control, Crookston, MN, 1995," *Arthropod Management Tests*, vol. 21, pp. 145-146.

Hedin, et al., "Physical and biological properties of the spinosyns: novel macrolide pest-control agents from fermentation," Phytochemicals for Pest Control, Chapter 11, 1995 *International Chemical Congress of Pacific Basin Societies*; ACS Symposium Series 658, pp. 144-153.

Boyd, "Impact of insecticides on predators of the soybean looper, Pseudoplusia inc, " *Dissertation*; UMI (9637762): [97pp]; The Louisiana State University and Agriculture.

Sears, et al., "Effects of various rates and combinations of insecticides on the control of Colorado potato beetle (CPB) (1995)," *Pest Management Research Report—Insects and Diseases*, ICAR: 86100104; pp. 159-161; Report No. 061 (1995).

J. M. Edwards, et al., "Potential of Spinosad as a Control Agent for Diptera," ESA Annual Meeting, Las Vegas, Nevada, Dec. 17-21 (1995).

* cited by examiner

POUR-ON FORMULATIONS

The present invention relates to non-irritant carriers or carrier blends suitable for use in pour-on formulations, the formulations themselves and to the use of those pour-on formulations in the control of external parasites in animals of agricultural worth including sheep, cattle, pigs, goats, camelids, horses and other small ruminants.

Animals of agricultural worth, such as sheep, cattle, horses, goats, pigs, other ruminants and camelids, are almost invariably subject to the activity of ectoparasites such as flies, ticks, lice and fleas. Such external parasites irritate the animals and can cause economic losses in the forms of poor quality hide, wool or sheep skin, reduced weight gain and even death as a result of the animal carrying harmful parasites.

It has long been common practice to control external parasites on sheep, cattle and other animals including goats, pigs and horses by the localised topical application of a pour-on formulation containing an active insecticide/parasiticide and a carrier/vehicle. A pour-on formulation is typically liquid and is usually applied to the exterior of an animal as a line or a spot, which then acts to protect the external surface of the animal against external parasites such as lice, keds, mites, ticks and flies.

Ideally, when the formulation is applied topically to a localised area, the ectoparasiticide migrates over the surface of the animal to protect its whole external surface area.

The carrier (also referred to herein as 'vehicle') present in such pour-on formulations is formulated to achieve good spread around the skin and/or penetration of the epidermis of the animal. To date, commercial pour-on formulations are suspensions, emulsifiable concentrates or solutions and are often comprised of at least one organic solvent. Solvents commonly used as carriers in such pour-on formulations include propylene glycol, paraffins, isoparaffins, aromatics, isopropyl myristate (IPM), glycol ethers, and alcohols such as n-propyl alcohol. U.S. Pat. No. 4,672,072 discloses a non-aqueous carrier comprising one or more organic solvents such as xylene, toluene, cyclohexanone and a glycol—such as ethylene glycol, polyethylene glycols, polypropylene glycols, propylene glycol, ethylene glycol-propylene glycol copolymers and alkyl ethers thereof. A preferred solvent system disclosed in U.S. Pat. No. 4,672,072 comprises 30–70 wt % xylene, 20–40 wt % cyclohexanone and 5–25 wt % vegetable oil. U.S. Pat. No. 5,045,536 discloses a pour-on formulation in which the solvent system comprises 80–98% w/v of a non-volatile oil and 2–20% w/v of a volatile silicone.

Unfortunately, the solvent systems utilised as carriers/vehicles in commercially available pour-on formulations may result in some form of tissue reaction which leads to discomfort to the animal and in many cases, damage to the hide, sheepskin or fleece and resultant economic loss. In particular, some breeds of sheep such as the Merino have very sensitive skins which react to the solvent systems in some commercially available pour-on formulations. For example, aromatics such as xylene and the paraffins produce tissue reactions such as dryness, redness and cracking of the skin.

U.K. Patent GB 2 110 091 B attempts to address the problems of skin reactions in sheep treated with pour-on formulations by formulating a composition in which the carrier/vehicle comprises a first solvent selected from the group consisting of alkoxylated $C_1$–$C_4$ alcohols and a second solvent selected from the group consisting of di ($C_1$–$C_6$ alkyl) esters of $C_2$–$C_6$ dicarboxylic acids or $C_2$–$C_6$ dihydric alcohols and $C_2$–$C_6$ carboxylate esters of alcohol alkoxylates. However, sensitive animal hide can still react adversely to such formulations.

Similarly, European Patent Publication No. 0 120 286 B1 addresses the irritancy or toxicity caused to animals by solvent systems in pour-on formulations by providing an active ectoparasiticide in a glycol or glycerol ester of a $C_8$–$C_{10}$ fatty acid. However, such oil-based formulations can still cause adverse epidermal reactions in animals topically treated with such formulations.

European Patent Publication No. 0 137 627 B1 discloses a pour-on formulation in which the active is an endoparasiticide and the carrier comprises at least one saturated aliphatic ester of a mono alkyl ether of a mono- or polyalkylene glycol such as 1-ethoxyprop-2-yl acetate and 2-(n-butoxy)ethyl butyrate. While the specification claims that such formulations are free from adverse skin reaction in treated sheep or cattle, it is noted that adverse epidermal reactions can still be observed, particularly in sheep with sensitive skin.

Accordingly, prior art pour-on formulations—even those promoted as non-irritant—have been found by the present inventors to cause pain and hide damage, and fleece damage in the case of sheep or other fleece bearing animals. Such formulations cause skin damage especially in sheep, which have very thin skin and are acutely susceptible to chemical skin damage.

Additionally, with conventional pour-on formulations 95–98% of the applied active ingredient remains at the site of application bound to the animal's fleece or hair, which results in a lack of efficacy.

This invention provides non-toxic and non-irritant carriers that can be used to prepare improved pour-on ectoparasiticidal formulations. The invention also provides these improved formulations, which are especially beneficial because they can be topically applied to animals of agricultural worth to control ectoparasites without causing adverse epidermal reaction in the animals. The invention also provides a method of controlling ectoparasites in an animal of agricultural worth by topically applying one of these non-irritant pour-on ectoparasiticidal formulations on the animal.

The word 'carrier' is used throughout the present specification to include carrier blends, that is mixtures of more than one substance.

The term "controlling" as used in this specification refers to preventing, ameliorating or eradicating the target ectoparasite.

Certain acronyms and abbreviations used throughout this specification are commonly used in this art and have the following meanings:

The term "Alcohol" refers to benzyl alcohol, propyl alcohol, diacetone alcohol or other suitable alcohol;

COI is a blend of isopropyl myristate and cetearyl octanoate, which are branched chain esters; it acts as an emollient and spreading agent;

DB is diethylene glycol n-butyl ether;

DPM is dipropylene glycol methyl ether;

GTCC is glyceryl tri caprylate/caprate, which is an excellent carrier or vehicle for active agents;

ICS is isocetyl stearate, which can be used as an emollient, lubricant and spreading agent;

IPM is isopropyl myristate, which has excellent spreading and emollient properties;

IPL is isopropyl laurate;

IPP is isopropyl palmitate;

OP is octyl palmitate or 2-ethylhexyl palmitate, which is an excellent lubricant;

OS is octyl stearate or 2-ethylhexyl stearate, which is also a lubricant;

OSU is dioctyl succinate or di-2-ethylhexyl succinate, which promotes wetting and spreading of lipophilic substances onto the skin;

PG is propylene glycol;

PMP is, which spreads rapidly and promotes wetting of other material;

SC is a suspension concentrate;

TPM is tripropylene glycol methyl ether; and

WG is wool grease.

In a first aspect, the invention provides a non-irritant topically acceptable carrier selected from the group consisting of:

a) i) at least one of TPM and DPM, and
   ii) at least one of alcohol, WG and PG, wherein (i) is present in an amount of at least about 60% wt of the carrier;

b) i) at least one of OP, OS and GTCC, and
   ii) at least one of OSU, IPM, COI, PMP, IPP, IPL, ICS, oleic acid and methyl oleate, and optionally including
   iii) at least one of alcohol, WG and PG, wherein (ii) is present in an amount of up to about 40% wt of the carrier; and c) i) at least one of OP, OS and GTCC, and
   ii) at least one of alcohol, WG and PG, wherein (i) is present in an amount of at least about 60% wt of the carrier.

In a second aspect, the invention provides a non-irritant pour-on formulation for controlling an external parasite in an animal of agricultural worth, said formulation including an ectoparasiticidal amount of an active agent and a topically acceptable carrier of the first aspect of the invention.

A third aspect of this invention provides a method of controlling an external parasite in an animal of agricultural worth, said method including topically applying an ectoparasiticidally effective volume of a pour-on formulation according to the second aspect of the invention to a localised area of the external surface of the animal.

Another aspect of this invention relates to the use of a carrier of the first aspect in a non-irritant pour-on formulation for controlling an external parasite in an animal of agricultural worth wherein the formulation also includes an effective amount of an ectoparasiticidal agent.

The invention is predicated upon a novel approach to developing carriers suitable for use in non-irritant and non-toxic pour-on formulations that are to be used for animals of agricultural worth, such as sheep, cattle, horses, goats and pigs. This approach involved determining the effects of a potential pour-on ingredient on the skin using a histopathological methodology rather than relying on clinical observation. Such a histopathological approach has resulted in the significantly improved pour-on formulations of this invention.

The carriers of the first aspect of this invention have several advantages. They are non-irritant and effective. They also have a satisfactory freezing point, suitable viscosity and are cost effective. They easily dissolve any active agent, are easy to use and provide superior operator safety.

The formulations prepared using these carriers (or vehicles) represent a great advance over currently available pour-on formulations which have been developed upon an ad hoc basis. Such a histopathological approach has allowed for the identification and elimination of ingredients (including those used in current pour-on formulations) that cause skin/hide damage on a pathological level and also has allowed for the accurate determination of what percentage of an irritant ingredient will not cause damage.

Further, the carriers and formulations of this invention promote the spread of active agent around the body and hence increase efficacy against ectoparasites which can be present on any part of the body.

Finally, the formulations of this invention require the presence of less active agent, thereby reducing wool and tissue residues and environmental contamination.

One preferred embodiment of the first aspect of this invention is a non-irritant, topically acceptable carrier selected from the group consisting of:

a) i) at least one of TPM and DPM, and
   ii) at least one of alcohol, WG and PG, wherein (i) is present in an amount of at least about 60% wt of the carrier; and b) i) at least one of OP, OS and GTCC, and
   ii) at least one of OSU, IPM, COI, PMP, IPP, IPL, ICS, oleic acid and methyl oleate, wherein (ii) is present in an amount of up to about 40% wt of the carrier.

In carrier (a), solvent (i) is typically present in an amount of at least about 70% wt of the carrier.

When (a)(ii) is an alcohol, it is typically benzyl alcohol or diacetone alcohol.

An example of carrier (a) is TPM/alcohol where TPM is present in an amount of at least about 60% wt of the carrier. A particularly suitable TPM/alcohol carrier is TPM/benzyl alcohol. Typically, a TPM/alcohol carrier is formulated having a TPM:alcohol ratio in the range of 60–95:40–5, and more typically 80:20.

In carrier (b), substance (ii) is typically present in an amount of up to about 30% wt of the carrier.

Examples of carrier (b) are: OP or OS/IPM/OSU where the combined amount of IPM and OSU is up to about 40% wt of the carrier; and GTCC/IPM/COI where the combined amount of IPM and COI is up to about 40% wt of the carrier. When the carrier is OP/IPM/OSU, the preferred ratio is a range of OP:IPM:OSU of 60–90:20–5:20–5, most preferably 70:15:15. When the carrier is a combination of GTCC/IPM/COI, the preferred ratio of GTCC:IPM:COI is in a range of 60–90:20–5:20–5, preferably 70:15:15.

Optionally, carrier (b) can include: iii) at least one of alcohol, WG and PG.

One embodiment of the second aspect of the invention, i.e., a pour-on formulation for control of an external parasite in an animal of agricultural worth, is a formulation that includes:

(a) from 0.1 to 40% by weight of at least one active agent selected from the group consisting of synthetic pyrethroids, organophosphates, macrocyclic lactones (avermectins/milbemycins), benzoylphenylureas (and other insect growth regulators) and spinosyns; and (b) from 60–99.9% by weight of a carrier of the first aspect of the invention.

More specifically, this embodiment provides a pour-on formulation for control of an external parasite in an animal of agricultural worth, said formulation including:

(a) from 0.1 to 40% by weight of at least one active agent selected from the group consisting of synthetic pyrethroids, organophosphates, macrocyclic lactones (avermectins/milbemycins), benzoylphenylureas (and other insect growth regulators) and spinosyns; and (b) from 60–99.9% by weight of a carrier selected from the group consisting of (1) TPM/alcohol, wherein the TPM is present in an amount of at least 60% by weight of the carrier; (2) OP/IPM/OSU wherein the combined amount of IPM/OSU is at least 40% by weight of the carrier; and (3) GTCC/IPM/COI wherein the combined amount of IPM/COI is at least 40% by weight of the carrier.

The pour-on formulations of this invention can be in the form of a liquid, powder, emulsion, foam, paste, aerosol, ointment, salve or gel. Typically, the pour-on formulation is liquid.

These pour-on formulations can be effectively applied to sheep, cattle, goats, other ruminants, camelids, pigs and horses. The formulations are particularly suitable to be applied to sheep, especially short wool sheep.

The pour-on formulations are applied locally to the external surface of an animal. Although they can be applied at any time, certain regimens are preferable. For example, when the formulations are applied to sheep, they are typically applied within 24 hours after shearing. The sheep are then usually treated each year after shearing. Fibre animals such as goats and camelids are also treated after shearing. Cattle are treated depending on the pest concerned, such as in autumn/winter for lice and in summer for flies.

The pour-on formulation is typically applied by pouring in one or several lines or in a spot on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race.

An effective amount of the pour-on formulation for topical application will depend on several factors, e.g. the animal being treated, the active agent in the formulation, and the specific formulation being used. Generally, the formulation should provide about 0.1–2000 mg of the active agent/kg of animal body weight.

The effective amount of formulation will vary depending on the animal being treated. For example, when the formulation is to be applied to a cow, it should provide about 100–2000 mg of the active agent. When it is to be applied to a sheep, it should provide about 20–1000 mg of the active agent.

The effective amount of active (ectoparasiticidal) agent in the formulation will depend on both the agent and the carrier. Examples of preferred amounts of active agents (per kg of animal body weight) are: about 300 mg of spinosad or 100 mg of ivermectin or 600 mg of benzoylphenylurea or 80 mg of zeta-cypermethrin, when these agents are formulated in OP/IPM/OSU or TPM/alcohol or GTCC/IPM/COI.

A pour-on formulation of this invention is generally formulated such that the active agent is present in a concentration of about 0.1–20% weight/volume, preferably about 0.5 to 5%, depending on the potency of the active agent. Typically, the formulation will contain one or more of the preferred active agents in the following concentrations (weight/volume):

zeta-cypermethrin: about 0.5%;
ivermectin: about 0.6%;
hexaflumuron: about 4–5%; and
spinosad: about 2%.

Typically, only a small volume of the pour-on formulation, such as in the order of 1–80 mL, is required in order to be effective against the external parasites. For larger animals such as cattle, a volume of 10–60 mL is preferred; and for smaller animals such as sheep, a volume of 5–20 mL is suitable.

In the pour-on formulations of this invention, the active/ectoparasiticidal agent can be a single insecticidal/ectoparasiticidal compound or a combination of two or more insecticidal/ectoparasiticidal compounds. The active agent is typically selected from the group consisting of spinosyns, synthetic pyrethroids, macrocyclic lactones, diamidides (formamidines) such as amitraz, thiazoles, dursban, carbamates, benzimidazoles, fipronil, imidacloprid, triazines, water-insoluble organo-phosphate compounds, propoxur, cabaryl, maldison, dimethoate, rotenone, piperonyl butoxide, *Bacillus thuringensis*, ronnel, crufomate, benzoylphenylureas and other insect growth regulators (IGR) such as hexaflumuron or insect development inhibitors (IDI), or related juvenile insect hormone analogues, including cyromazine and dicyclanil.

A particularly useful spinosyn is spinosad.

Examples of synthetic pyrethoids are cyhalothrin, bioresmethrin, bifenthrin, pyrethrins, permethrin, biopermethrin, phenothrin, alphamethrin, barthrin, deltamethrin, phthalthrin, cypermethrin, dimethrin, flumethrin, resmethrin, fluvalinate, allethrin, cismethrin, cyfluthrin, indothrin, cyphenothrin, cyclethrin, tetramethrin, tralomethrin, sumithrin, tralocythrin, fenpropanate and fenvalerate. Particularly useful pyrethrins are alpha-cypermethrin and zeta-cypermethrin.

Examples of macrocyclic lactones are ivermectin, abamectin, moxidectin, doramectin, eprinomectin, and milbemycin.

Examples of water-insoluble organo-phosphate compounds are tetrachlovinphos, chlorpyriphos methyl, pyrimiphos methyl, chlorpyriphos, diazinon, trichlorphos, fenchlorphos, coumaphos, crotoxyphos, chlofenvinephos, dichlofenvinphos, dichlorfenthion, quinthiophos, propetamphos, famphur, bromophos ethyl, ethion, and dioxathion.

Examples of benzoylphenylureas are lufenuron, diflubenzuron, triflumuron and fluazuron.

More typically, the active agent is selected from the group consisting of spinosad, zeta-cypermethrin, ivermectin and hexaflumuron.

The carriers of this invention are non-aqueous. The active agent is suspended, dissolved or dispersed in the carrier. The carrier promotes the penetration of the active agent through the animal's coat and spread of the agent over the skin.

In addition to the carrier and the active agent, the pour-on formulations of this invention can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention typically include an antioxidant, such as BHT (butylated hydroxytoluene). The antioxidant is generally present in amounts of at 0.1–5% (wt/vol).

Some of the formulations require a solubilizer, such as oleic acid, to dissolve the active agent, particularly if spinosad is used.

Common spreading agents used in these pour-on formulations are: IPM, IPP, caprylic/capric acid esters of saturated $C_{12}$–$C_{18}$ fatty alcohols, oleic acid, oleyl ester, ethyl oleate, triglycerides, silicone oils and DPM.

The pour-on formulations of this invention are prepared according to known techniques. Where the pour-on is a solution, the parasiticide/insecticide is mixed with the carrier or vehicle, using heat and stirring where required. Auxiliary or additional ingredients can be added to the mixture of active agent and carrier, or they can be mixed with the active agent prior to the addition of the carrier. If the pour-on is an emulsion or suspension, these formulations are similarly prepared using known techniques.

A general procedure for preparing these formulations involves these steps:

1) Weigh out the desired weight of technical active agent;
2) Add 0.1–1% w/v BHT or other appropriate antioxidant;
3) If the agent is spinosad, add oleic acid (4 times the weight of spinosad used), and dissolve by stirring;
4) Make up the desired volume by adding a carrier of this invention;
5) Mix by stirring and gently heating if necessary—to up to 50 degrees C.; and
6) Dispense into impervious containers and protect from light.

This invention further provides a method of controlling an external parasite in an animal of agricultural worth, said method including topically applying an ectoparasiticidally effective volume of a pour-on formulation according to the second aspect of the invention to a localised area of the external surface of the animal. The target external parasites include lice, ticks, mites, biting flies, carnivorous flies and fleas. Animals of agricultural worth include cattle, sheep, goats, pigs, horses, camelids and other ruminants.

More specifically, the method of this invention can be used on sheep: to control ked (*Melophagus ovinus*), chewing louse (*Bovicola ovis*), sucking louse (*Linognatus pedalis, L. africanus, L. stenopsis*), sheep scab mite (*Psoroptes ovis*), itch mite (*Psorergates ovis*), mange mite (*Chorioptes ovis*), screw worms (*Cochliomyia* spp., *Chrysomya* sp., *Wohlfahrtia* spp.), ticks (*Boophilus* spp., *Ixodes* spp., *Haemophysalis* spp., *Ambylomma* spp., *Dermacentor* spp., *Hyalomma* spp., *Rhipicephalus* spp.), nasal bot flies (*Oestrus ovis*) and blowflies (*Lucilia, Calliphora, Phormia, Protophormia* spp.);

on goats: to control chewing louse (*Bovicola limbata, B. crassiceps, B. caprae*) and sucking louse species (*Linognathus* spp.);

on camelids: to control chewing lice (*Bovicola breviceps*);

on cattle: to control sucking louse (*Linognathus vituli, Haematopinus eurysternus, Solenopotes capillatus*) and chewing louse (*Bovicola bovis*), flies (e.g., *Musca domestica, Haematobia irritans, Stomoxys calcitrans*), screw worms (*Chrysomya bezziana, Cochliomyia hominivorax*), midges, mosquitos, mites (*Chorioptes bovis, Sarcoptes bovis, Psorpotes ovis, Demodex bovis*), and ticks (*Boophilus* spp, *Ixodes* spp, *Haemophysalis* spp, *Amblyomma* spp, *Dermacentor* spp. *Hyalomma* spp, *Rhipicephalus* spp, *Otobius megnini*);

on horses: to control ticks, mites (*Chorioptes equi, Psoroptes equi, Sarcoptes equi, Demodex equi*), chewing and sucking lice (*Bovicola equi, Haematopinus asini*), fleas, Dipteran species (*Culicoides* spp, *Simulium* spp and other flies); and on pigs: to control ticks, mites (including *Sarcoptes suis, Demodex suis*), lice (*Haematopinus* spp), fleas and Dipteran fly species.

The formulation is applied to the dorsal midline of the animal, from the poll to the base of the tail. Preferably, the formulation is applied using an applicator, usually a self-filling dosing gun with a nozzle to dispense a narrow or wide band or lines of formulation along the back. The formulation is applied at 0.2 to 1 mL per kilogram of body weight or unit of surface area. Alternatively, a set volume is applied to each bodyweight class, e.g., 10 mL for sheep or animals less than 30 kg, 15 mL for animals weighing 31–50 kg, and 20 mL for animals weighing 51+kg. In larger animals, for example in cattle, a typical volume would be 30 mL for animals less than 250 kg, 45 mL for animals weighing 250 to 400 kg and 60 mL for animals of 400+kg in weight. The formulation can also be applied from other containers or vessels as required.

Sheep and other fibre producing animals should be treated within 24 hours after shearing or fibre collection. Cattle, horses and other animals should be treated so as to ensure maximum impact on the pest to be controlled. For example, cattle should be treated for lice control in autumn and/or winter. Nuisance or biting fly treatment is applied when flies begin to cause irritation. This invention is illustrated in a non-limiting manner by reference to the following Examples.

EXAMPLE 1

Pour-On Carrier/Vehicle Sheep Skin Irritation Studies

Studies were conducted to investigate and characterise the changes occurring in Merino sheep skin following the application of a range of candidate pour-on formulation components in order to discern safe carriers. Chemicals, emollients, wool grease derivatives and a wide range of formulations were applied (in 1 mL volumes) to each of 18 sites on the back and flanks of 15 recently shorn Merino sheep.

In the first study, skin samples were collected at necropsy 3½ weeks after application. In subsequent studies, skin samples were collected 2 weeks after application. Standard haematoxylin and eosin stained sections were prepared from each piece of treated skin. A histological scoring system was devised to allow comparison of treatments. Each skin was assessed for the degree of hyperkeratosis, acanthosis and inflammatory cell infiltrate of the superficial dermis and given a rating score from 0–15. A score of 0=no change through to a score of 15 for very severe damage. Normal skin scored 2–4, >4 was abnormal and >7 was very abnormal. Treatments yielding a score ≤4.5 were considered safe.

Table 1 summarizes the results of these studies.

TABLE 1

| Mean skin irritation scores | |
|---|---|
| Chemical | Score |
| PMP | 9 |
| cetearyl octanoate | 4.3 |
| IPM | 8 |
| OP | 3.3 |
| OSU | 4.8 |
| GTCC | 2 |
| lanolin oil/IPM (80:20) | 7.5 |
| GTCC/IPM (80:20) | 2.5 |
| OP/IPM (80:20) | 2.5 |
| GTCC/COI (80:20) | 3 |
| OP/OSU (80:20) | 4.5 |
| DB | 7 |
| DPM | 4 |
| TPM | 3 |
| Diacetone alcohol | 2 |
| TPM/diacetone alcohol (80:20) | 2.5 |
| OP/IPM/OSU (70:15:15) | 3.2 |

TABLE 1-continued

Mean skin irritation scores

| Chemical | Score |
|---|---|
| TPM/benzyl alcohol (80:20) | 2.7 |
| untreated | 2.5 |

A small experiment was conducted to investigate the pathology over time following application of IPM. It was applied to 2 separate sites on 1 sheep on 1, 2, 4, 7, 10 and 14 days before slaughter.

These studies showed that, despite careful daily observation of the skin, some chemicals caused severe histological dermatitis in the absence of grossly observable changes. IPM caused severe dermatitis. Adding small percentages of other emollients or wool grease failed to make IPM non-irritant. Reducing the IPM percentage to 20% could yield a non-irritant formulation as long as the other components were non-irritant. Several other excipients were also highly irritant—such as PMP, C8–C10 methyl esters, methyl oleate, DB, 2-octyl-dodecanol and propylene glycol dicaprylate dicaprate. Other excipients and mixtures of excipients caused mild to moderate dermatitis—such as cetearyl octanoate, DPM, propoxy 15 stearyl alcohol, ICS and OSU. Some mixtures were non-irritant—such as OP/IPM (80:20); GTCC/OP (80:20); OP/IPM/OSU (70:15:15); GTCC/IPM/COI (70:15:15); TPM/benzyl alcohol (80:20) and several mixtures incorporating wool grease derivatives. GTCC, OP, diacetone alcohol, liquid wool grease, lanolin oil, and TPM were non-irritant.

A commercial formulation of deltamethrin in cyclohexane caused moderate dermatitis. This formulation was reported to cause scab formation on the skin, leading to damage detectable in tanned wool skins (Britt, Cotton, Trask and Pitman, 1984, *Aust vet J*, 61, 329–330). The pathology described in that paper was similar in type and pattern to that seen associated with the same formulation in these studies, but was milder than the severe dermatitis associated with several vehicles investigated in these studies.

Examples 2–11 describe in vivo formulation comparison and efficacy studies.

Trials were conducted to assess the comparative efficiency of certain pour-on formulations of this invention and commercially available pour-on formulations in the control of external parasites in sheep.

EXAMPLE 2

Evaluation of Wool Grease Formulations and IPM for the Control of *Bovicola ovis* using Zeta-Cypermethrin and Spinosad The purposes of this study were to evaluate wool grease as a formulation to deliver spinosad, to determine the dose required to kill 100% of lice in sheep and to evaluate the suitability of the formulation to deliver zeta-cypermethrin, compared with an isopropyl myristate (IPM) formulation.

Sheep were heavily infested with the highly synthetic pyrethroid (SP) resistant, Hartley strain of lice. Sheep were shorn, lice counted and sheep allocated to ten groups of six sheep, each divided into three groups of two per treatment. All sheep were treated at the rate of 2 mL of test formulation/10 kg of body weight. Treatments were, respectively: wool grease only; 2 mg/kg deltamethrin and 4 mg/kg alphacypermethrin in commercial formulations; spinosad in wool grease at 0.08 mg/kg, 0.4 mg/kg, 2 mg/kg and 10 mg/kg; zeta-cypermethrin in wool grease at 0.66 mg/kg and 2 mg/kg; and spinosad in IPM at 0.4 mg/kg. Lice numbers were counted weekly for eight weeks.

At eight weeks: 2 mg/kg deltamethrin gave 8% efficacy; 4 mg/kg alphacypermethrin gave 9% efficacy; 0.66 mg/kg zeta-cypermethrin gave 0% efficacy; 2 mg/kg zeta-cypermethrin gave 43% efficacy; 0.08, 0.4, 2 and 10 mg/kg spinosad in wool grease gave 42%, 54%, 98% and 99.9% efficacy, respectively; and 0.4 mg/kg spinosad in IPM gave 85% efficacy.

There were no significant differences in efficacy at eight weeks between zeta-cypermethrin in wool grease and deltamethrin and alphacypermethrin in the commercial pour-ons tested; however, zeta-cypermethrin (2 mg/kg) in wool grease gave better lice control than the commercial pour-ons for the first 5 weeks. Spinosad in IPM gave better control of sheep lice than spinosad in the wool grease gave at comparable dose rates.

EXAMPLE 3

Evaluation of Spinosad in a Variety of Carriers as a Pour-On Formulation for the Control of *Bovicola ovis* on Sheep The aim of this study was to select the most efficacious of a range of eight formulations that were selected on the basis of safety, physical properties, efficacy, cost and theories of dermal insecticide spread.

Each formulation was prepared to provide spinosad at a dose of 0.4 mg/kg and applied at a rate of 1 mL/5 kg of body weight. Groups of lousy sheep housed indoors (6 sheep per group) were treated with spinosad formulated in these carriers: IPM containing 0.6% oleic acid (IPM), GTCC/IPM/COI (70:15:15), OP/IPM/OSU (70:15:15), TPM/WG/GTCC (60:20:20), OP/IPM (80:20), TPM/OSU (80:20), GTCC/OP (80:20) and an aqueous formulation.

Five of the formulations, IPM, GTCC/IPM/COI, OP/IPM/OSU, TPM/WG/GTCC and the aqueous formulation, all gave about 90% efficacy by the end of the study. OP/IPM was inferior to the others and was eliminated. TPM/OSU and GTCC/OP were also somewhat less effective than the rest. The TPM/WG/OSU formulation was eliminated because WG-containing formulations cause dirty discolouration of the wool in sheep run outdoors. IPM alone was not a practical formulation due to skin irritation.

The best formulations, in order of cost from cheapest to most expensive, were: aqueous, OP/IPM/OSU and GTCC/IPM/COI.

EXAMPLE 4

Determination of the Therapeutic Efficacy and Dose Titration of Spinosad in a Pour-On Formulation for the Control of *Bovicola ovis* on Sheep This study was carried out to select the dose of spinosad required to eradicate sheep body lice when applied as a pour-on in OP/IPM/OSU (70:15:15) containing 5% oleic acid, and to compare the efficacy of spinosad at 0.4 mg/kg in a suspension concentrate (SC) formulation applied as a pour-on with that of the pour-on organic solvent formulation. The spinosad formulations were applied at 1 mL/5 kg and at 0, 0.2, 0.4, 0.8, 1.6 and 3.2 mg/kg to 6 groups of 6 recently shorn sheep that were housed outdoors for 6 weeks.

The results observed with the OP/IPM/OSU/oleic acid formulation are summarized in Table 2:

TABLE 2

Comparison of Efficacy of Various Dosage Levels of Spinosad Administered in an OP/IPM/OSU Pour-On Formulation

| Spinosad Dosage (mg/kg) | Efficacy (%) at Day 41 |
| --- | --- |
| 0.2 | 37 |
| 0.4 | 46 |
| 0.8 | 78 |
| 1.6 | 37 |
| 3.2 | 93 |

In the SC formulation spinosad at 0.4 mg/kg gave 65% efficacy.

EXAMPLE 5

Diffusion of $^{14}$C-Zeta-Cypermethrin on Sheep Skin in a Variety of Carriers

This study compared the amount and rate of diffusion of $^{14}$C-labelled zeta-cypermethrin from the dorsal midline of sheep, when applied in wool grease, in an aqueous formulation and in a range of test carriers.

Five formulations containing 10 mg/mL zeta-cypermethrin spiked with 100 Ci [$^{14}$C] zeta-cypermethrin were prepared using the following carriers: wool grease (1), 100 g/L emulsifiable concentrate (EC) diluted 1:10 in water (2), IPM (3), OS (4), and GTCC (5).

Each formulation was applied to the backline of three sheep at 1 mL/5 kg body weight. Wool was collected from three 12×12-mm squares chosen at random, along meridian lines drawn 2, 7.5 and 15 cm down the side of each sheep from the backline. The wool samples were collected at 1, 2, 4, 8, 11 and 14 days after treatment, and each day's samples were pooled. The clipped areas were also swabbed. At day 14 after treatment, the wool at the site of application was collected and back and perirenal fat samples were collected. The quantity of zeta-cypermethrin in each sample was measured by liquid scintillation counting.

At most meridians and at most times IPM gave the greatest spread of zeta-cypermethrin and wool grease the least. In the wool-grease formulations, the amount of zeta-cypermethrin present continued to increase with time only at the 2-cm meridian. The quantity of zeta-cypermethrin measured at all meridians increased with time following IPM. OS and GTCC gave modest spread, but the data did not allow determination of whether spread was continuing. The EC gave little spread, and movement of zeta-cypermethrin reached a plateau after 2 weeks. IPM caused a severe scabbing/crusting of the skin at the site of application.

The experiment was concluded at 2 weeks post-treatment. Wool grease and the EC formulation gave poor spread, GTCC and OS gave better spread and IPM gave the best spread of zeta-cypermethrin of the vehicles tested.

EXAMPLE 6

Evaluation of Zeta-Cypermethrin in a Variety of Carriers, as a Pour-On Formulation for the Control of *Bovicola ovis* on Sheep These studies were devised to determine the efficacy of zeta-cypermethrin (at 2 mg/kg of body weight) in several nonaqueous formulations, and a commercial formulation of deltamethrin, on sheep infested with a severely synthetic pyrethroid (SP) resistant (Hartley) strain and a moderately SP resistant (Claremont) strain of *Bovicola ovis*. Some additional studies were undertaken with susceptible and slightly resistant lice to determine whether zeta-cypermethrin was able to kill lice under optimum conditions.

The nonaqueous formulations tested were: OP/IPM (80:20); 2) GTCC/OP (80:20); 3) WG/C8-10 methyl esters/OP/GTCC [20% WG, 20% esters and 60% of OP/GTCC (80:20)]; 4) 20% WG and 80% GTCC/OP (80:20); and 5) 85% GTCC/OP (80:20) and 15% WG.

Against lice with high and moderate levels of resistance to the SPs, no treatment gave satisfactory lice control. Increasing the volume of formulation applied, but keeping the dose constant, led to a slight increase in efficacy against the moderately resistant strain. Zeta-cypermethrin eradicated lice on sheep infested with the susceptible strain and gave excellent control against a mildly resistant strain.

None of the formulations was significantly superior. The liquid wool-grease-containing formulations produced a very unsightly dirty mark in the wool along the treated area that would not be acceptable to farmers.

The OP/IPM or GTCC/OP formulations appeared to provide a good starting point to find a useful zeta-cypermethrin sheep pour-on formulation.

EXAMPLE 7

Evaluation of Zeta-Cypermethrin in a Variety of Carriers, as a Pour-On Formulation for the Control of *Bovicola ovis* on Sheep Example 6 revealed that zeta-cypermethrin at 2 mg/kg did not give adequate control against SP-resistant strains of *Bovicola ovis*, but did control SP-susceptible lice. This study evaluated various zeta-cypermethrin formulations for their effectiveness in controlling sheep body lice.

Five formulations of zeta-cypermethrin (Treatments 3–9) were compared to a commercial suspension concentrate (SC) formulation of alphacypermethrin for efficacy to treat moderately SP-resistant lice in sheep. The formulations were tested as follows:

| Treatment | Carrier | Dosage (mg/kg)[a] |
| --- | --- | --- |
| 1 | Control | 0 |
| 2 | Alphacypermethrin SC | 4 |
| 3 | OP/IPM (80:20) | 2 |
| 4 | " | 4 |
| 5 | GTCC/OP (80:20) | 2 |
| 6 | " | 4 |
| 7 | TPM/WG/GTCC (60:20:20) | 4 |
| 8 | OP/IPM/OSU (70:15:15) | 4 |
| 9 | TPM/benzyl alcohol (80:20) | 4 |

[a]The 2 mg/kg dosage was applied at 10 g/L; and the 4 mg/kg dosage was applied at 20 g/L.

None of the zeta-cypermethrin formulations tested eradicated lice. The TPM/benzyl alcohol formulation gave the lowest counts following treatment. The OP/IPM at 2 mg/kg and OP/IPM/OSU at 4 mg/kg formulations gave the next best control. The OP/IPM and GTCC/OP formulations at 4 mg/kg were similar in efficacy to that of the alpha-cypermethrin suspension concentrate formulation.

These results indicated that the TPM/benzyl alcohol or OP/IPM/OSU formulations delivering 4 mg/kg zeta-cypermethrin would control strains of lice exhibiting zero to low resistance to SPs. Since zeta-cypermethrin at 2 mg/kg in an inferior formulation (Example 6) eliminated susceptible lice, a TPM/benzyl alcohol or OP/IPM/OSU formulation delivering 4 mg/kg zeta-cypermethrin should give excellent control of SP-susceptible lice.

EXAMPLE 8

Small Scale Trial to Evaluate Spinosad in a Variety of Carriers, as a Pour-On Formulation for the Control of *Bovicola ovis* on Sheep In Example 3, lousy sheep housed indoors were treated with 0.4 mg/kg spinosad formulated in OP/IPM/OSU and lice numbers declined by 90%. When a similar formulation containing 5% oleic was applied to sheep housed outdoors, efficacy was only 46% (Example 4). This experiment explored the effects of an outdoor environment and oleic acid on the efficacy of a spinosad-containing pour-on formulation against lice.

Spinosad was formulated at 2 g/L in OP/IPM/OSU (70:15:15). Each formulation was applied at 1 mL/5 kg (or 0.4 mg/kg) to groups of two louse-infested sheep. There was an outdoor untreated control group. One indoor and one outdoor group were treated with OP/IPM/OSU as in Example 3. Another outdoor group was treated with OP/IPM/OSU plus 5% oleic acid as in Example 4. A fourth outdoor group was treated with OP/IPM/OSU plus 5% oleic acid plus the antioxidant BHT.

The indoor treated sheep had a 77% percent reduction in lice numbers after 28 days; this result was similar to the effect observed in Example 3. The outdoor untreated group had 0% reduction in counts. Both outdoor groups treated with oleic acid-containing formulations had 40–50% reduction in counts, which was similar to the efficacy seen in Example 4. BHT had no effect on efficacy.

EXAMPLE 9

Evaluation of Spinosad in a Variety of Carriers, as a Pour-On Formulation for the Control of *Bovicola ovis* on Sheep.

This study assessed the effectiveness of spinosad in an OP/IPM/OSU formulation, a TPM/benzyl alcohol formulation, a suspension concentrate and two other aqueous formulations to control lice outdoors. Another purpose was to confirm that outdoor conditions reduce the efficacy of any formulation, as compared to indoor conditions. The study also assessed the efficacy of UV absorbers/blockers on outdoor efficacy. Merino sheep were used, and the study ran for 6 weeks.

All formulations contained spinosad at 2 mg/kg (1 mL/5 kg body weight). Each of the five formulations was given with a UV blocker present. In addition, the OP/IPM/OSU formulation without UV blocker was tested indoors and outdoors.

The nonaqueous formulations contained 1% spinosad and were formulated and tested as follows:

| Group | Carrier | Ratio | Housed |
|---|---|---|---|
| 2 | OP/IPM/OSU | 70:15:15 | indoors |
| 3 | OP/IPM/OSU/zinc oxide/IPP/BHT | 63:13:13:6.6:2.9:1 | outdoors |

-continued

| Group | Carrier | Ratio | Housed |
|---|---|---|---|
| 4 | OP/IPM/OSU | 70:15:15 | outdoors |
| 5 | TPM/benzyl alcohol/zinc oxide/IPP/BHT | 73:18:6.6:2.9:1 | outdoors |

The OP/IPM/OSU formulation delivering 2 mg/kg spinosad gave 99.96% efficacy indoors; this result was significantly superior to that seen with the same formulation outdoors with or without a UV blocker. In the groups housed outdoors, each formulation was similar in effectiveness, although the OP/IPM/OSU formulation was the most effective. UV blockers did not significantly increase efficacy.

EXAMPLE 10

Evaluation of a Variety of Pour-On Carriers with Ivermectin and Hexaflumuron for the Control of *Bovicola ovis* on Sheep Several previous experiments (Examples 3, 4, 6, 8 and 9) have shown that an OP/IPM/OSU (70:15:15) formulation is both safe for sheep skins and an effective vehicle to deliver zeta-cypermethrin and spinosad to control lice in sheep. Similarly, carriers based on TPM, such as TPM/benzyl alcohol (80:20) are safe and effective. The aim of this study was to demonstrate that these formulations could deliver other classes of ectoparasticides, such as macrocyclic lactones (ivermectin) and insect growth regulators (hexaflumuron).

In the study, groups of 4 Merino sheep, housed indoors, were treated with ivermectin (40 mg/sheep) or hexaflumuron (600 mg/sheep) in OP/IPM/OSU (70:15:15) or TPM/benzyl alcohol (80:20). Sheep were treated with 20 mL of formulation applied to the backline. Six sheep were left untreated as controls. Lice were counted every 2 weeks for 12 weeks.

Tables 3 and 4 summarize the results of these studies.

TABLE 3

Lice counts in sheep at day 0 and 14, 28, 42, 56 and 85 days after treatment with ivermectin[a]

| Group | Day 0 | Day 14 | Day 28 | Day 42 | Day 56 | Day 85 |
|---|---|---|---|---|---|---|
| Control | | | | | | |
| Mean | 618.7 | 540.0 | 463.7 | 611.0 | 562.8 | 533.0 |
| Geo Mean | 608.8 | 518.4 | 414.5 | 586.5 | 513.8 | 461.4 |
| Op/IPM/OSU[b] | | | | | | |
| Mean | 706.0 | 2.3 | 0.5 | 0 | 0 | 0 |
| Geo Mean | 698.4 | 1.3 | 0.3 | | | |
| TPM/Benzyl Alcohol[c] | | | | | | |
| Mean | 606.0 | 9.5 | 4.3 | 0.5 | 0.5 | 0 |
| Geo Mean | 564.9 | 6.3 | 1.9 | 0.4 | 0.3 | |

[a]40 mg/sheep
[b]70:15:15
[c]80:20

TABLE 4

Lice Counts in sheep at day 0 and 14,
28, 42, 56 and 85 days after treatment
with hexaflumaron[a]

| Group | Day 0 | Day 14 | Day 28 | Day 42 | Day 56 | Day 85 |
|---|---|---|---|---|---|---|
| Control | | | | | | |
| Mean | 618.7 | 540.0 | 463.7 | 611.0 | 562.8 | 533.0 |
| Geo Mean | 608.8 | 518.4 | 414.5 | 586.5 | 513.8 | 461.4 |
| OP/IPM/OSU[b] | | | | | | |
| Mean | 690.0 | 86.3 | 37.8 | 14.5 | 6.0 | 2.3 |
| Geo Mean | 683.1 | 39.0 | 8.6 | 3.3 | 2.9 | 1.1 |
| TPM Benzyl Alcohol[c] | | | | | | |
| Mean | 672.3 | 324.5 | 110.8 | 46.8 | 44.3 | 16.8 |
| Geo Mean | 656.7 | 266.9 | 91.0 | 31.7 | 32.4 | 10.3 |

[a]600 mg/sheep
[b]70:15:15
[c]80:20

EXAMPLE 11

Evaluation of Spinosad in Two Pour-On Formulations and Ivermectin as a Pour-On for the Control of *Bovicola ovis* on Sheep Housed Outdoors This study evaluated the efficacy of spinosad to eradicate lice in sheep when administered in two pour-on vehicles. It also determined the effect of increasing dose or volume on efficacy and whether the incorporation of UV blockers/absorbers increases efficacy. The study further evaluated the efficacy of ivermectin to eradicate lice when administered in a pour-on formulation to sheep housed outdoors.

Spinosad was administered in OP/IPM/OSU (70:15:15) at 2 and 10 mg spinosad/kg body weight, with and without UV blockers, and applied at 2 mL/5 kg of body weight. Ivermectin was administered at 40 mg/sheep in 20 mL of OP/IPM/OSU (70:15:15). Spinosad was also administered in an aqueous formulation at 2, 10 and 50 mg/kg without UV blockers and applied at 1 mL/5 kg. In addition, the 2 mg/kg formulation was applied at 1 mL/kg. All treatments were applied as a broad band along the backline. The study ran for 6 weeks.

These results were observed:
A) Spinosad in OP/IPM/OSU: at 10 mg/kg, with or without UV blockers, it eradicated lice outdoors; at 2 mg/kg, it gave 85 to 98% efficacy.
B) Spinosad in aqueous formulation: at 50 mg/kg, it eradicated lice; at 10 mg/kg, it gave 98% efficacy; at 2 mg/kg, it gave 74% efficacy when applied at 1 mL/5 kg and 61% efficacy when applied at 1 mL/kg.
C) Ivermectin in OP/IPM/OSU: at 40 mg/sheep, it gave 96% efficacy.
D) The use of UV blockers or increasing the volume applied did not increase efficacy.

EXAMPLE 12

Physical Characteristics of Various Formulations

The physical characteristics of various individual solvents and solvent combinations were determined. Table 5 summarizes the results of these determinations.

TABLE 5

Summary of formulation properties and freezing points

| Vehicle | Physical Properties |
|---|---|
| IPM | Freeze −2 to −6°C., penetrates + spreads, modifies heavy oils |
| GTCC | Freeze −5 to −13°C., safe, solvent/diluent |
| OP or OS | Freeze 3 to −4°C., spreads, lubricant |
| OSU | Freeze 0 to 15°C., good spreader, wets |
| COI | Freeze 0°C., water resistant, good wetter + spreader |
| TPM | Freezes <<−15°C. |
| OP/IPM (80:20) | Freezes −4 to −7°C. |
| OP/OSU (80:20) | Freezes −7 to −10°C. |
| GTCC/IPM (80:20) | Freezes < <10°C. |
| TPM/2-octyl dodecanol (80:20) | Freezes −15°C. |
| TPM/diacetone alcohol (80:20) | Freezes <−15°C. |

What is claimed is:

1. A non-irritant pour-on formulation for control of an external parasite on an animal of agricultural worth comprising 0.1 to 40% by weight of at least one spinosyn; and a non-irritant topically acceptable carrier selected from the group consisting of:
   a) i) tripropylene glycol methyl ether, and
      ii) at least one of benzyl alcohol and diacetone alcohol, wherein (i) is present in an amount of at least about 60% wt of the carrier;
   b) i) at least one of octyl palmitate, octyl stearate and glyceryl tri caprylate/caprate, and
      ii) at least one of dioctyl succinate, isopropyl myristate, cetearyl octanoate, propylene glycol 2 myristyl ether propionate, isopropyl palmitate, isopropyl laurate, isocetyl stearate, oleic acid and methyl oleate, and optionally including
      iii) at least one of alcohol and propylene glycol, wherein (ii) is present in an amount of up to about 40% wt of the carrier; and
   c) i) at least one of octyl palmitate, octyl stearate and glyceryl tri caprylate/caprate, and
      ii) at least one of benzyl alcohol, diacetone alcohol and propylene glycol,
   wherein (i) is present in an amount of at least about 60% wt of the carrier.

2. A formulation of claim 1 wherein the ratio of tripropylene glycol methyl ether:alcohol is in the range of 60–95:40–5.

3. A formulation of claim 2 wherein the ratio of tripropylene glycol methyl ether:alcohol is 80:20.

4. A formulation of claim 1 wherein the carrier is selected from (b).

5. A formulation of claim 4 wherein (i) is octyl palmitate or octyl stearate.

6. A formulation of claim 5 wherein (ii) comprises isopropyl myristate and dioctyl succinate.

7. A formulation of claim 6 wherein the ratio of octyl palmitate:isopropyl myristate:dioctyl succinate is 60–90: 20–5:20–5.

8. A formulation of claim 7 wherein the ratio is 70:15:15.

9. A formulation of claim 4 wherein (i) is glyceryl tri caprylate/caprate and (ii) comprises isopropyl myristate and a blend of isopropyl myristate and cetearyl octanoate.

10. A formulation of claim 9 wherein the ratio of glyceryl tri caprylate/caprate:isopropyl myristate:blend of isopropyl myristate and cetearyl octanoate is in a range of 60–90: 20–5:20–5.

11. A formulation of claim 10 wherein the ratio is 70:15:15.

12. A non-irritant pour-on formulation for control of an external parasite on an animal of agricultural worth, according to claim 1, wherein said spinosyn is spinosad.

13. A method of controlling an external parasite on an animal of agricultural worth, comprising topically applying an ectoparasiticidally effective volume of a pour-on formulation of claim 12.

14. A non-irritant pour-on formulation for control of an external parasite on an animal of agricultural worth, according to claim 2, wherein said spinosyn is spinosad.

15. A method of controlling an external parasite on an animal of agricultural worth, comprising topically applying an ectoparasiticidally effective volume of a pour-on formulation of claim 14.

16. A non-irritant pour-on formulation for control of an external parasite on an animal of agricultural worth, according to claim 3, wherein said spinosyn is spinosad.

17. A method of controlling an external parasite on an animal of agricultural worth, comprising topically applying an ectoparasiticidally effective volume of a pour-on formulation of claim 16.

18. A non-irritant pour-on formulation for control of an external parasite on an animal of agricultural worth, according to claim 4, wherein said spinosyn is spinosad.

19. A method of controlling an external parasite on an animal of agricultural worth, comprising topically applying an ectoparasiticidally effective volume of a pour-on formulation of claim 18.

20. A non-irritant pour-on formulation for control of an external parasite on an animal of agricultural worth, according to claim 5, wherein said spinosyn is spinosad.

21. A method of controlling an external parasite on an animal of agricultural worth, comprising topically applying an ectoparasiticidally effective volume of a pour-on formulation of claim 20.

22. A non-irritant pour-on formulation for control of an external parasite on an animal of agricultural worth, according to claim 6, wherein said spinosyn is spinosad.

23. A method of controlling an external parasite on an animal of agricultural worth, comprising topically applying an ectoparasiticidally effective volume of a pour-on formulation of claim 22.

24. A non-irritant pour-on formulation for control of an external parasite on an animal of agricultural worth, according to claim 7, wherein said spinosyn is spinosad.

25. A method of controlling an external parasite on an animal of agricultural worth, comprising topically applying an ectoparasiticidally effective volume of a pour-on formulation of claim 24.

26. A non-irritant pour-on formulation for control of an external parasite on an animal of agricultural worth, according to claim 8, wherein said spinosyn is spinosad.

27. A method of controlling an external parasite on an animal of agricultural worth, comprising topically applying an ectoparasiticidally effective volume of a pour-on formulation of claim 26.

28. A non-irritant pour-on formulation for control of an external parasite on an animal of agricultural worth, according to claim 9, wherein said spinosyn is spinosad.

29. A method of controlling an external parasite on an animal of agricultural worth, comprising topically applying an ectoparasiticidally effective volume of a pour-on formulation of claim 28.

30. A non-irritant pour-on formulation for control of an external parasite on an animal of agricultural worth, according to claim 10, wherein said spinosyn is spinosad.

31. A method of controlling an external parasite on an animal of agricultural worth, comprising topically applying an ectoparasiticidally effective volume of a pour-on formulation of claim 30.

32. A non-irritant pour-on formulation for control of an external parasite on an animal of agricultural worth, according to claim 11, wherein said spinosyn is spinosad.

33. A method of controlling an external parasite on an animal of agricultural worth, comprising topically applying an ectoparasiticidally effective volume of a pour-on formulation of claim 32.

* * * * *